(12) United States Patent
Tam (10) Patent No.: US 8,192,400 B2
(45) Date of Patent: Jun. 5, 2012

(54) PNEUMATIC INJECTION DEVICE (76) Inventor: Weng Kong Tam, Kowloon (HK)

( * ) Notice: Subject to any disclaimer, the term of this patent is extended or adjusted under 35 U.S.C. 154(b) by 185 days.

(21) Appl. No.: 12/542,846

(22) Filed: Aug. 18, 2009

(65) Prior Publication Data
US 2011/0045433 A1 Feb. 24, 2011

(51) Int. Cl.
A61M 37/00 (2006.01)

(52) U.S. Cl. ............... 604/131; 604/140; 433/82

(58) Field of Classification Search ........... 433/82; 604/140–143, 93.01, 185, 121, 131
See application file for complete search history.

(56) References Cited

U.S. PATENT DOCUMENTS

5,019,037 A * 5/1991 Wang et al. .............. 604/23
7,195,610 B1 * 3/2007 Flachbart .............. 604/99.01
* cited by examiner

Primary Examiner — Christopher D Koharski
(74) Attorney, Agent, or Firm — Kevin J. McNeely; McNeely, Hare & War, LLP (57) ABSTRACT The invention relates to a pneumatic injection device adapted to be connected with an air outlet of a dental chair for providing a compressed air flow, comprising: an injection unit comprising a unit body having a proximal end, a distal end and a cavity between the proximal and distal ends for receiving a dental cartridge, wherein the distal end has an injection needle connector for connecting a needle, and the proximal end is connected to an air seal adaptor in an airtight relationship; an output pressure selector having an output end connected air-tightly to the other end of the air seal adaptor; an air releasing means having an output end connected air-tightly to an input end of the output pressure selector; and an input pressure adjustor having an output end connected air-tightly to an input end of the air releasing means, an input end for connection to the air outlet of the dental chair.

13 Claims, 5 Drawing Sheets

Fig. 6

PNEUMATIC INJECTION DEVICE

FIELD OF THE INVENTION

The present invention relates to an injection device, and more particularly to a pneumatic injection device adapted to be connected with an air outlet of a dental chair for providing a compressed air flow, which is particularly suitable for the injection of anesthetics for dental procedures.

BACKGROUND OF THE INVENTION

The administration of local anesthetics is an indispensable step of dental practice, however, it is always not a good experience to both dentists and patients. There exist various types of dental anaesthetic injection device in the market, among others, a manual (thumb-palm) driven injection device and a computer based injection device are well known in the art.

The injection device of manual driven type may cause occupational injuries to the dentists at their fingers joints exerting forces while controlling the plunger of the syringe holder. In addition, it is hard for the dentists to maintain the stability of an injecting hand while the same hand is required to exert full effort in manipulating the injection device or the plunger of the syringe holder thereof. As a result, injection of the anaesthetic by using such an injection device is hard to proceed smoothly in producing a painless injection. Also, the patients find agony in receiving a dental local anaesthesia, which ends up in low patients' return rate and compliance.

The injection device of computer based type is expensive and computer dependent, which causes additional costs and renders operational difficulties to the dentists, because most of the dentists are now practicing without a computer and in turn do not get used to computer operations, although such computer based systems can bring the advantages of automation and precise dosage control of the injection. Consequently, the majority of dental professionals worldwide are still using a traditional thumb-and-palm grasping cartridge-syringe system out of financial consideration and due to its low technical requirements.

Because of the mechanism of the traditional anaesthetic injection device described above, most of the dentists have an early onset of occupational health problems such as Carpal Tunnel Syndrome. The frequent wearing of thumb and palm tendon leads the dentists to the development of tendonitis, an illness that is preventable if attended earlier.

Another drawback of the traditional anaesthetic injection device is its limited ability in successful controlling of the pressure, rate, volume and the tissue penetration of the injection. This leads to an agony of pain sensation applied to the patients while receiving the injection of anesthetics.

Therefore, there exists a need for developing a pneumatic anaesthetic delivery system which is easy to install and operate and structurally simple, and which does not require a computer nor any additional electronic device. Such a system is able to not only save the dentists from career trauma, but also alleviate pain in the patients.

SUMMARY OF THE INVENTION

An object of the invention is to overcome at least partly the above defects in the prior art by providing a pneumatic anaesthetic injection device, which is relatively simple in configuration, low in cost, and easy to install and operate.

Accordingly, the invention provides a pneumatic injection device adapted to be connected with an air outlet of a dental chair for providing a compressed air flow, comprising:

an injection unit comprising a unit body having a proximal end, a distal end and a cavity between the proximal and distal ends for receiving a dental cartridge, wherein the distal end has an injection needle connector for connecting a needle, and the proximal end is connected to an air seal adaptor in an airtight relationship;

an output pressure selector having an output end connected air-tightly to the other end of the air seal adaptor;

an air releasing unit having an output end connected air-tightly to an input end of the output pressure selector; and an input pressure adjustor having an output end connected air-tightly to an input end of the air releasing unit, an input end for connection to the air outlet of the dental chair.

Optionally, a control unit is arranged on the unit body of the injection unit for controlling flow rate and pressure of the compressed air that flows into the injection unit.

According to one embodiment of the present invention, a movable rubber stopper is arranged in the cartridge in the vicinity of the proximal end of the unit body of the injection unit for urging the injection of the anesthetic inside the cartridge by the air, and the air seal adaptor is further provided with a silicon pad for providing an air seal contact with the cartridge to facilitate the injection of the anesthetic. Preferably, the cartridge protrudes beyond the proximal end of the unit body by 1 mm to 5 mm, which ensures that the silicon pad is directly contacting with and applying a pressure on the cartridge.

In one preferred embodiment of the present invention, the output pressure selector is a three-way valve having an air conduit for passage of the air, and a turning adjustor in communication with the air conduit for providing the desirable pressure of the air that comes into the injection unit. Preferably, the turning adjustor is formed as a cylindrical valve having air tracts of different sizes in operable communication with the air conduit for controlling the air at different pressures. More preferably, the output pressure selector is disposed such that the tuning adjustor can be manipulated easily by a finger.

According to another embodiment of the present invention, the air releasing unit comprises a primary air inlet passage, a secondary air inlet passage in communication with the primary air inlet passage, an air outlet passage operably in communication with the primary air inlet passage, and an air exhaust passage in communication with the secondary air inlet passage, wherein a floating valve, a silent mesh, and a spring coil having one end attached to the floating valve and the other end attached to the silent mesh are mounted centrally and axially in the air exhaust passage.

According to still another embodiment of the present invention, the input pressure adjustor comprises a pressure gauge and a pressure adjustment element for adjusting the pressure of the compressed air to a desirable range. The input end of the input pressure adjustor preferably is fitted with a plug and play tubing connector for connection to the air outlet of the dental chair.

According to the invention, the connections among the unit body of the injection unit, the air seal adaptor, the output pressure selector, the air releasing unit and the input pressure adjustor may be accomplished in a threaded manner or in a plug and play manner.

According to embodiments of the present invention, standard cartridges and needles could be used as the cartridge and the needle of the pneumatic injection device.

The invention provides a forceless pneumatic driven local anaesthetic injection device which takes replacement of the traditional force demanding thumb-palm grasping injection system. With the injection device of the invention, the performance of the dentists would not be hindered by occupational injuries in the long run. The pneumatic injection device of the invention is characterized by a delicate control mechanism over the pressure, rate, and volume of injection, allowing for patients' higher compliance in receiving treatment, thereby enhancing the quality of life of patients. The pneumatic injection device is easy to install and operate, user-friendly in design (i.e. pen-grip model) and does not require any software or hardware installation. Another advantage of the pneumatic injection device is its compatibility with currently available standard drug cartridges and needles to which no modification is necessary.

The invention provides for the first time an all-purpose dental chair air-driven and non-computer based injection device in dentistry. The injection device works independently and does not require any new type of drug container and/or injection needle. No extra electricity socket or electric supply is required for the pneumatic injection of the invention which is driven by compressed air from a medical air outlet of the dental chair that is an indispensable instrument in the current practice of the dentists.

According to the invention, the injection device can find a wide range of applications in specific dental anaesthetic procedures, which include but not limiting to infiltration injection, intraosseous injection, intra-ligament injection, anterior middle superior alveolar block (AMSA) injection, palatal anterior superior alveolar block (P-ASA) injection, periodontal ligament (PDL) injection, block injection and the like.

BRIEF DESCRIPTION OF THE DRAWINGS

The further objects, features, characteristics and effects of the invention will be illustrated in more details by way of examples with reference to the accompany drawings, wherein.

DETAILED DESCRIPTION OF THE PREFERRED EMBODIMENTS

While this invention is illustrated and described in preferred embodiments, the pneumatic injection device may be produced in many different configurations, sizes, forms and materials.

Figure 1:
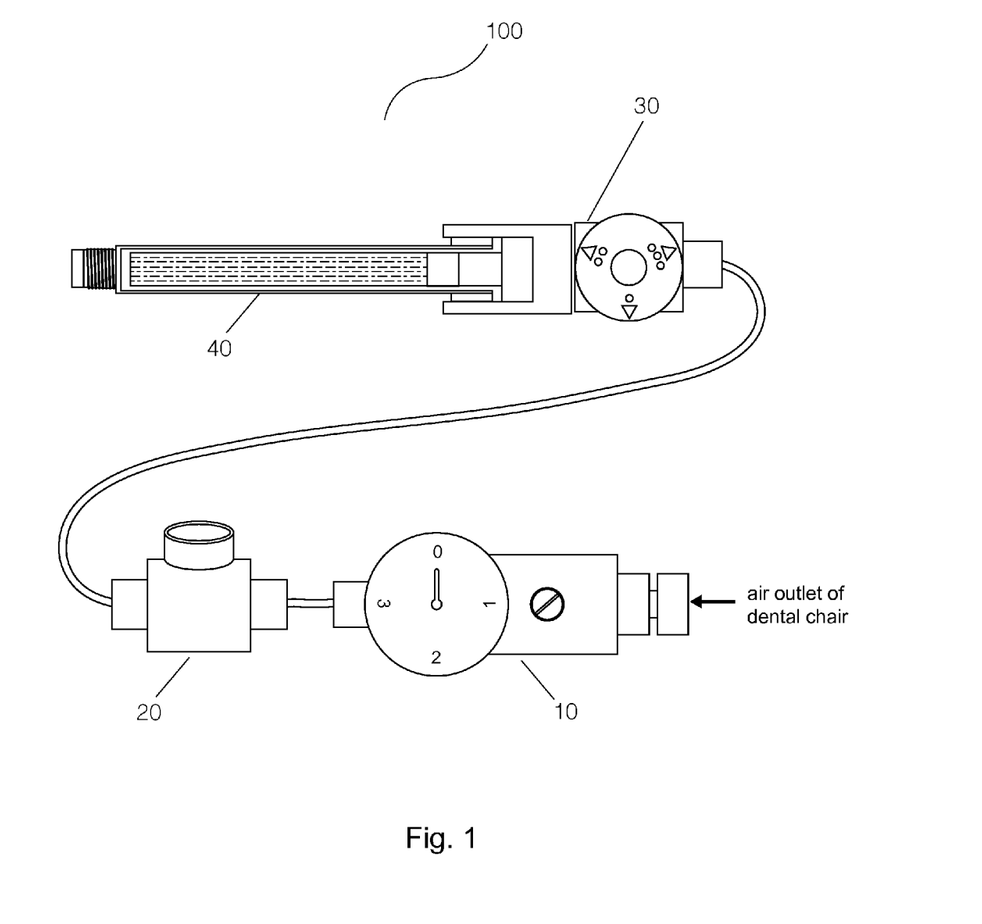
FIG. 1 is a schematic view of a pneumatic injection device constructed consistent with a first embodiment of the invention.

Referring to FIG. 1, a schematic view of a pneumatic injection device 100 constructed consistent with a first embodiment of the invention is illustrated. The pneumatic injection device 100 is adapted for use with a dental chair having an air outlet for providing a compressed air flow. As shown in FIG. 1, the pneumatic injection device 100 comprises an input pressure adjustor 10 having an input end fitted with a connector (not shown) for connection to the air outlet, and the pressure of the compressed air flow can be adjusted by the input pressure adjustor 10 to maintain a predetermined pressure range at its output end. The pneumatic injection device 100 comprises an air releasing unit 20 having an input end connected airtightly to the output end of the input pressure adjustor 10 for a better and controlled release of pressure, and having an output end connected airtightly to an input end of an output pressure selector 30. The pneumatic injection device 100 further comprises an injection unit 40 that is connected to the output end of the output pressure selector 30 in an airtight relationship, which will be described hereinbelow. Thus, a path for the passage of the air flow is created by the input pressure adjustor 10—the air releasing unit 20—the output pressure selector 30—the injection unit 40. FIG. 1 also shows that a dental cartridge containing an anaesthetic and an injection needle are mounted in the anaesthetic injection unit 40, allowing for administration of the anaesthetic by the compressed air flow. According to the invention, the dental cartridge may be a tailor made dental anaesthetic cartridge or a standard (1.8 ml) one, and so does the injection needle.

Figure 2A:
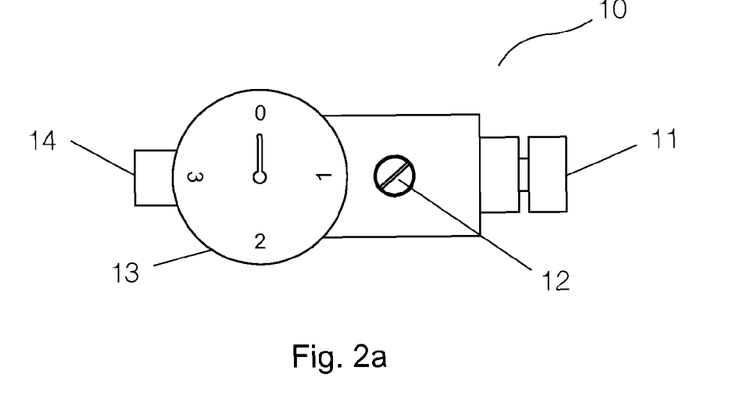
FIG. 2*a* is a schematic top view of an input pressure adjustor used in the pneumatic injection device shown in FIG. 1.
Figure 2B:
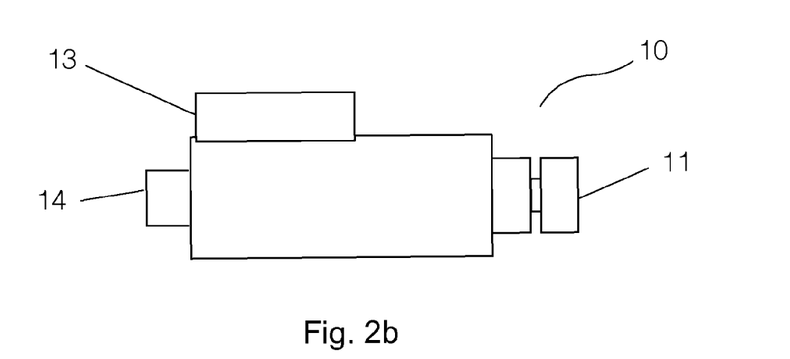
FIG. 2*b* is a schematic front view of the input pressure adjustor shown in FIG. 2*a*.

FIGS. 2*a* and 2*b* illustrate the input pressure adjustor 10 used in the pneumatic injection device 100 shown in FIG. 1. The input pressure adjustor 10 comprises an input connector 11, a pressure adjustment member 12 and a pressure gauge 13 in series connection. The input connector 11 may be a plug and play tube connector for ease of connection with the air outlet of the dental chair. The pressure adjustment member 12 may be formed as a pressure adjusting screw, a pressure adjusting valve or the like for regulation and determination of the output pressure to a desirable range. The pressure gauge 13 provides the reader of the pressure for the dentists. The input pressure adjustor 10 further comprises an output connector 14 which is connected to the air releasing unit 20. In this embodiment, the output connector 14 is a plug and play tube connector for easy and instant connection with the air releasing unit 20.

Figure 3A:
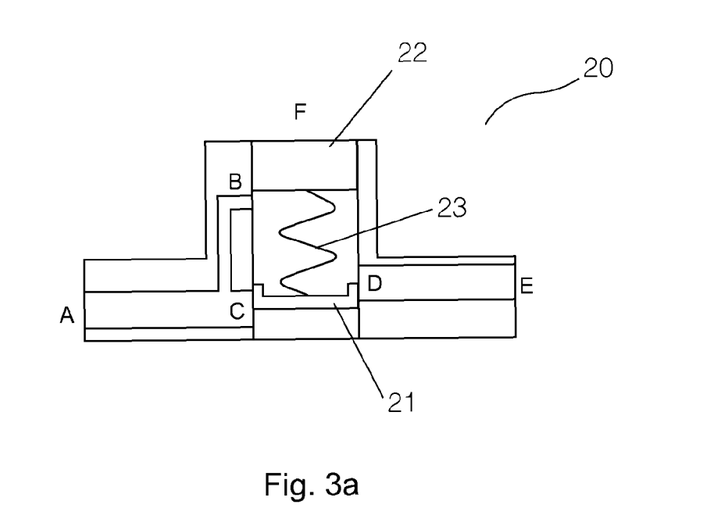
FIGS. 3*a*-3*e* are schematic views of an air releasing unit used in the pneumatic injection device shown in FIG. 1.
Figure 3B:
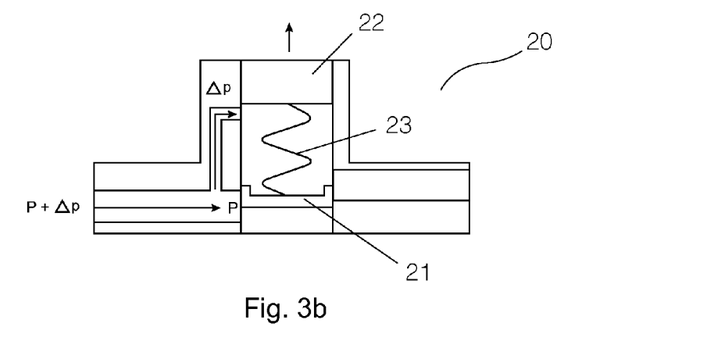
Figure 3C:
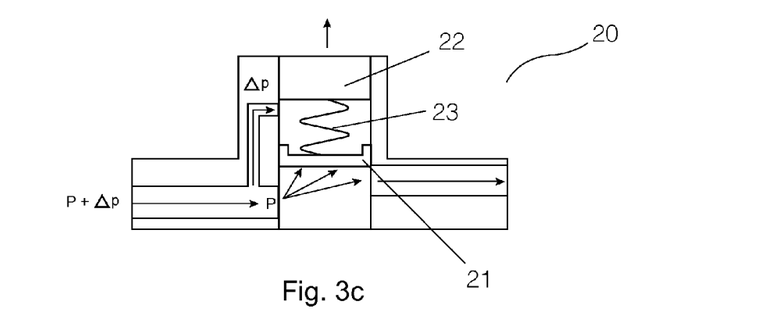
Figure 3D:
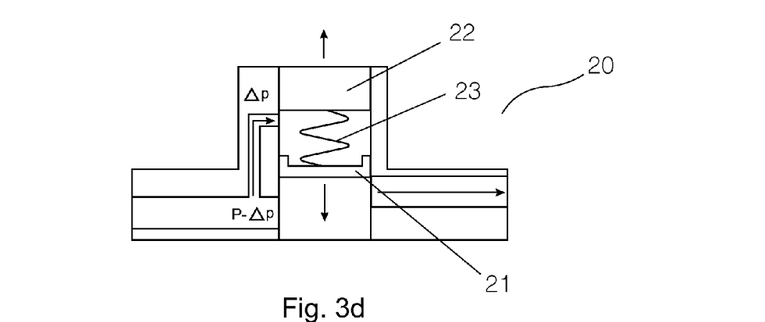
Figure 3E:
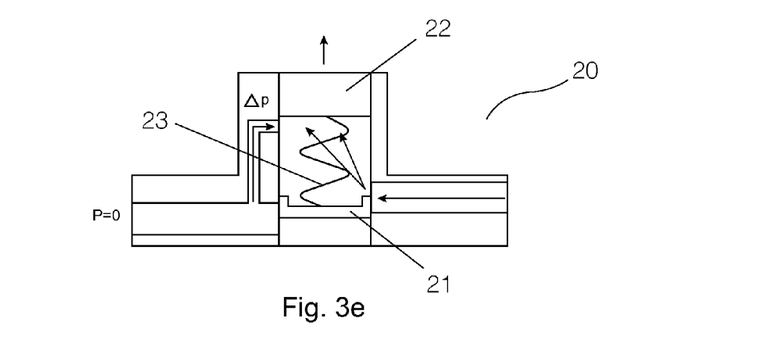

The air releasing unit 20 is illustrated in FIGS. 3*a*-3*e*, which comprises a primary air inlet passage A-C, a secondary air inlet passage A-B, an air outlet passage D-E, and an air exhaust passage F. The secondary air inlet passage A-B is in communication respectively with the primary air inlet passage A-C and the air exhaust passage, and the primary air inlet passage A-C is operably in communication with the air outlet passage D-E. In the air exhaust passage, a floating valve 21, a silent mesh 22 and a spring coil 23 having one end attached to the floating valve 21 and the other end attached to the silent mesh 22 are mounted centrally and axially. The floating valve 21 is able to move vertically along with a combined effect of an upward force originating from the compressed air coming out from the primary air inlet passage A-C and a spring force originating from the spring coil 23. With the movement of the floating valve 21, the primary air inlet passage A-C is communicable or uncommunicable with the air outlet passage D-E. The floating valve 21 is positioned vertically such that the primary air inlet passage A-C is operably not in communication with the air outlet passage in a released position of the floating valve, and such that the primary air inlet passage A-C is operably in communication with the air outlet passage D-E in a compressed position of the floating valve. In this embodiment, the floating valve 21 is a disc-type member of U-shaped cross section. If the compressed air flow is shut off or the pressure leakage from the air exhaust passage to the ambient takes place, the floating valve 21 is held in the released position where the primary air inlet passage A-C is not in communication with the air outlet passage D-E. When the compressed air flows into the primary air inlet passage A-C, the floating valve is urged to move upward to the compressed position where the primary air inlet passage A-C is in intercommunication with the air outlet passage D-E from which the air comes out from the air releasing unit 20, as shown in FIG. 3c. At the beginning of shutting off of the compressed air flow, the air flow in the air releasing unit 20 would gradually escape through the secondary air inlet passage A-B to the air exhaust passage F and then to the ambient, in this case, a pressure difference is generated between the primary air inlet passage A-C and the air outlet passages D-E, allowing for the downward movement of the floating valve 21 from the compressed position to the released position under the spring force of the spring coil 23, as shown in FIG. 3d. This makes the disconnection of the primary air inlet passage A-C from the air outlet passage D-E again, and at the end of the shutting off of the compressed air flow, the compressed air flow remaining in the pneumatic injection device would readily release to the ambient through the air outlet passage D-E and the air exhaust passage, as shown in FIG. 3e. In this embodiment, the silent mesh 22 is arranged at an output end of the air exhaust passage for reducing the noise caused by the releasing of the air to the ambient. According to the invention, the air releasing unit 20 serving as a quick exhaust valve in the pneumatic injection device can be separately provided or integrated with the input pressure adjustor 10.

Figure 4A:
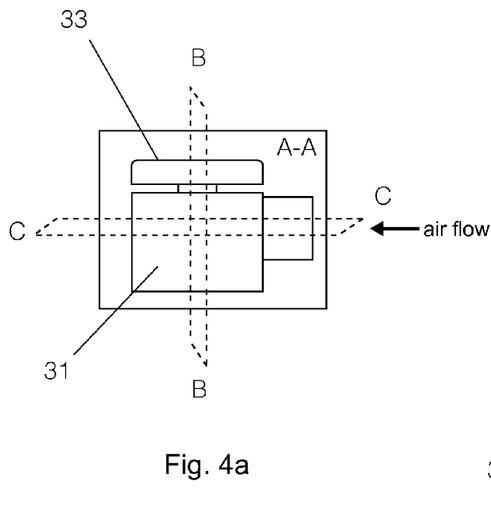
FIG. 4*a* is a schematic front view of an output pressure selector used in the pneumatic injection device shown in FIG. 1.
Figure 4B:
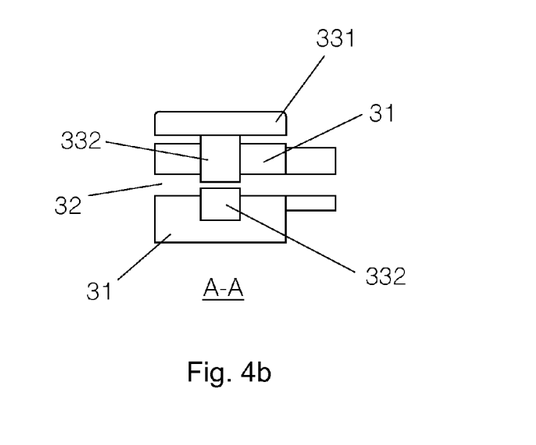
FIG. 4*b* is a schematic view of the output pressure selector taken along plane A-A of FIG. 4*a*.
Figure 4C:
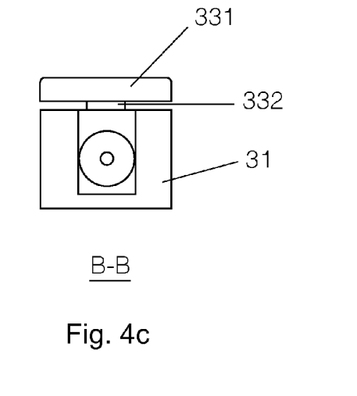
FIG. 4*c* is a schematic view of the output pressure selector taken along plane B-B of FIG. 4*a*.
Figure 4D:
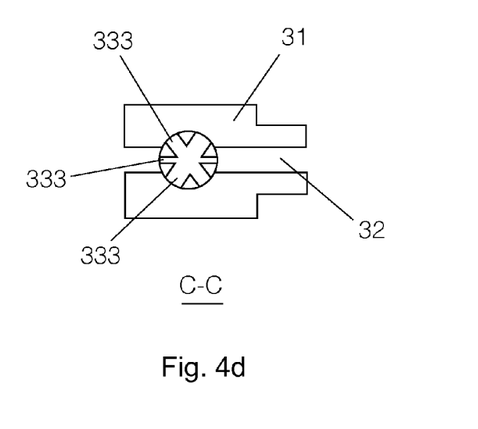
FIG. 4*d* is a schematic view of the output pressure selector taken along plane C-C of FIG. 4*a*.

The output pressure selector 30 is illustrated in FIGS. 4a-4d. In this embodiment, the output pressure selector 30 is a mechanical multi-way selector, such as a three-way valve adapted for manual switching by a finger of an operator. The output pressure selector 30 comprises a tubular body 31 having a transverse air conduit 32 for passage of the compressed air flow, and an opening perpendicularly extending from a top of the tubular body 31 to and through the transverse air conduit 32 for receiving a tuning adjustor which is used to control the air flow for providing the desirable pressure of the air that comes into the injection unit. The tuning adjustor is positioned such that it can be manipulated by a finger such as a thumb. In this embodiment, the turning adjustor is a cylindrical valve 33 which is constructed to have three air tracts 333 of different diameters in operable intercommunication with the transverse air conduit 32, enabling to alter the pressure of the compressed air flow passing through the transverse air conduit 32 by guiding the compressed air flow through the respective air tracts of different diameters. It should be understood that the air tracts may be of different cross sections and/or different sizes when necessary, provided that a desirable pressure difference is created across the ends of the transverse air conduit 32. In this embodiment, the cylindrical valve 33 has a T-shaped cross section and consists of an upper circular plate portion 331 located over the tubular body 31 and a lower cylinder portion 332 received in the opening of the tubular body 31. As shown in FIG. 4d, the central axes of the air tracts are located on a same plane in the lower cylinder portion and the air tracts are intercommunicable with each other and selectable by rotation of the circular plate portion 331. Turning the upper circular plate portion 331 allows a corresponding air tract to be in intercommunication with the transverse air conduit 32 to create a pressure difference across two ends of the transverse air conduit, thereby providing a desirable output pressure at the output end of the output pressure selector 30. It would be appreciated that a plurality of air tracts of different diameters can be located on different planes in the lower cylinder portion 332 and are switchable by vertically moving the lower cylinder portion up and down for allowing the compressed air flow to pass through a specific air tract for a desirable output. It can be understood that use of the output pressure selector 30 allows for a quick switching among the different output pressures to reach a required injection speed of the anesthetic. The output pressure selector 30 can be separately provided or integrated with other parts of the pneumatic injection device. Preferably, the output pressure selector 30 is integrated with the injection unit 40 for ease of manual operation by a finger of an operator.

Figure 5:
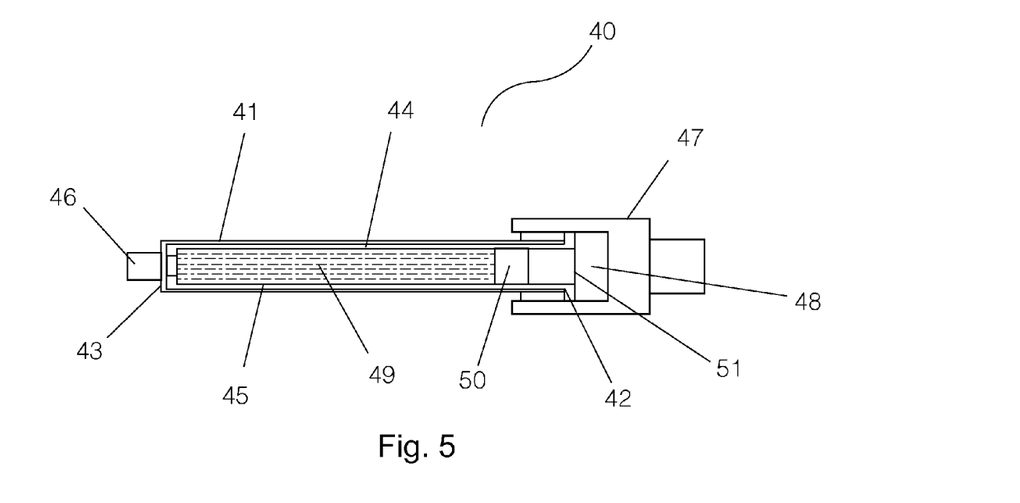
FIG. 5 is a schematic view of an injection unit used in the pneumatic injection device shown in FIG. 1.

Illustrated in FIG. 5 is the injection unit 40 which comprises a unit body 41 having a proximal end 42, a distal end 43 and a cavity 44 between the proximal and distal ends for receiving a dental anesthetic cartridge 45 containing an anaesthetic 49. In this embodiment, the injection unity 40 is a syringe, and the unity body 41 is a syringe body. The distal end 43 has an injection needle connector 46 for connecting to a needle, and the proximal end 42 is connected to an air seal adaptor 47 in an airtight relationship. The other end of the air seal adaptor 47 is connected airtightly to the output end of the output pressure selector 30 for allowing the passage of the air into the dental anesthetic cartridge 45 to urge the injection of the anesthetic contained therein. The air seal adaptor 47 is provided with a silicon pad 48 in order for directly contacting with and applying a pressure against an end 51 of the cartridge 45 in an air-seal fashion to facilitate the injection of the anesthetic. The silicon pad 48 has a through hole for the passage of the air. A movable rubber stopper 50 is arranged in the cartridge 45 in the vicinity of the proximal end 42 of the syringe body. Preferably, the end 51 of the cartridge 45 protrudes beyond the proximal end 42 of the syringe body by 1 mm to 5 mm, in order to ensure that the silicon pad 48 is directly contacting with and applying a pressure against the end 51 of the cartridge 45. Standard and tailor made cartridges and needles are used in this embodiment.

After the pneumatic injection device is assembled, actuation of a compressed air source allows the compressed and pressure-adjusted air flow to pass through the input pressure adjustor 10, the air releasing unit 20, the output pressure selector 30 and the air seal adaptor 47 in sequence. The compressed air emitting from the air seal adaptor 47 would drive the rubber stopper 50 from the end 51 of the anesthetic cartridge 45 received in the injection unit 40 towards the injection needle connector 46 to enable the anesthetic to be injected through the injection needle in a predetermined rate.

As shown in FIGS. 1-5, the connections among the unit body 41 of the injection unit 40, the air seal adaptor 47, the output pressure selector 30, the air releasing unit 20 and the input pressure adjustor 10 are accomplished airtightly in a plug and play manner or in a snap-fit manner. It should be appreciated that threaded connections among these parts are possible, and a screw type of an injection unit is shown in FIG. 6.

Figure 6:
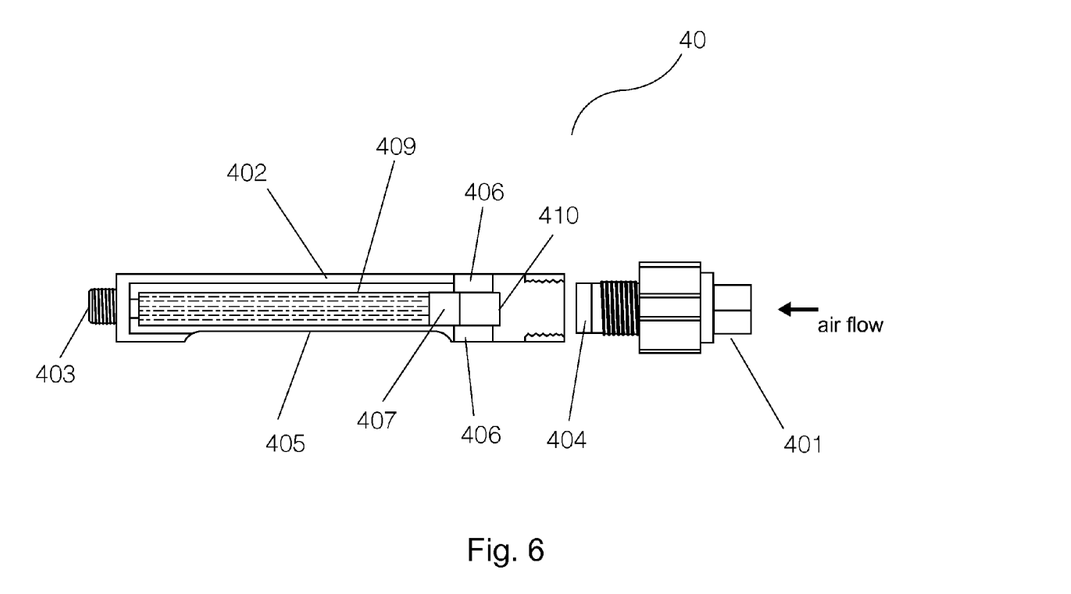
FIG. 6 is a schematic view of an injection unit according to a second embodiment of the invention.

Referring now to FIG. 6, an alternative embodiment of the injection unit 40 is illustrated, which is sized and shaped for holding and manipulation by hand. This injection unit 40 comprises a detachable air seal adaptor 401, a unit body 402 and an injection needle connector portion 403 which are thread-connected in series and are intercommunicable with each other by an internal passage defined by these parts. As mentioned in the above embodiment, the air seal adaptor 401 is airtightly connected at its input end to the output end of the output pressure selector 30 and connected at its output end to the input end of the unit body 402 in a threaded manner to ensure an air tight connection therebetween. An inner flange 406 is arranged in the vicinity of the input end of the unit body 402, which forms an air tight connection with an outer circumferential surface of a conventional or tailor made anaesthetic cartridge 409 received in the unit body 402. At the output end of the air seal adaptor 401 is a silicone pad 404 having a through hole for the passage of the air. The silicon pad 404 is able to directly contacting with a proximal end 410 of the anaesthetic cartridge 409 in an air seal fashion, which end 410 protrudes beyond the unity body 402, as shown in FIG. 6. The compressed air coming out from the silicon pad 404 would push a movable rubber stopper 407 arranged in the cartridge 409, and thus the anesthetic towards the injection needle connector portion 403. An injection indicator 405, such as an opening in this embodiment, is optionally provided on the unit body 402 to allow for observing the status of the anaesthetic cartridge 409 or for indicating the progress of injection. Alternatively, the unit body 402 can be made of a transparent material for visualization of the injection progress. The output end of the unit body 402, i.e. the injection needle connector portion 403, is connected to a conventional or tailor made injection needle in a threaded manner. In operation, the air seal adaptor 401 is first detached from the anaesthetic injection unit 40, followed by insertion of the anaesthetic cartridge 409 into the unit body 402 and then mounting of the air seal adaptor 401 on the unit body 402 and the mounting of an injection needle on the injection needle connector portion 403. As described above, upon actuation of a compressed air source, the compressed and pressure-adjusted air flow entering into the air seal adaptor 401 and emitting from the through hole of the silicone pad 404 would drive the rubber stopper 407 from the proximal end 410 of the cartridge 409 towards the injection needle connector portion 403 to enable the anesthetic to be injected through the injection needle in a predetermined rate.

Thus, the invention provides a pneumatic injection device which takes advantage of using an air outlet of a dental chair equipped by every dental practitioner as a compressed air source, without the need for additional power source. Various pneumatic parts, such as the input pressure adjustor 10, the air releasing unit 20, the output pressure selector 30, are used to control the pressure, flow rate and volume of injection in a subtle manner. A dentist can slightly touch the pneumatic injection device to trigger the injection of anesthetic by his or her finger for a desirable operation. This is quite different from the traditional systems requiring forceful gripping in order to activate movement of a piston. Once the compressed air is actuated, the rubber stopper inside the cartridge would be driven to move to urge the injection of the anaesthetic into a patient's tissue through pneumatic force, eliminating the need of software or hardware installation associated with the use of a computer. Another advantage of the pneumatic injection device of the invention is that it is compatible with anaesthetic drug vials and market needle tips available in existing market. With the compression of the anaesthetic by compressed air, the injection of the anaesthetic is steady and under a smooth discrete stepped dosing control according to the invention.

Having sufficiently described the nature of the present invention according to some preferred embodiments, the invention, however, should not be limited to the structures and functions of the embodiments and drawings. It is stated that insofar as its basic principle is not altered, changed or modified it may be subjected to variations of detail. Numerous variations and modifications that are easily obtainable by means of the skilled person's common knowledge without departing from the scope of the invention should fall into the scope of this invention.

What is claimed is:

1. A pneumatic injection device adapted to be connected with an air outlet of a dental chair for providing a compressed air flow, comprising:
an injection unit comprising a unit body having a proximal end, a distal end and a cavity between the proximal and distal ends for receiving a dental cartridge, wherein the distal end has an injection needle connector for connecting a needle, and the proximal end is connected to an air seal adaptor in an airtight relationship;
an output pressure selector having an output end connected air-tightly to the other end of the air seal adaptor;
an air releasing unit having an output end connected airtightly to an input end of the output pressure selector, wherein the air releasing unit comprises a primary air inlet passage, a secondary air inlet passage in communication with the primary air inlet passage, an air outlet passage operably in communication with the primary air inlet passage, and an air exhaust passage in communication with the secondary air inlet passage, and wherein a floating valve, a silent mesh, and a spring coil having one end attached to the floating valve and the other end attached to the silent mesh are mounted centrally and axially in the air exhaust passage; and
an input pressure adjustor having an output end connected air-tightly to an input end of the air releasing unit, an input end for connection to the air outlet of the dental chair.

2. The pneumatic injection device according to claim 1, wherein a movable rubber stopper is arranged in the cartridge in the vicinity of the proximal end of the unit body of the injection unit for urging the injection of the anesthetic inside the cartridge by the air.

3. The pneumatic injection device according to claim 2, wherein the air seal adaptor is provided with a silicon pad for providing an air seal contact with the cartridge.

4. The pneumatic injection device according to claim 3, wherein the cartridge protrudes beyond the proximal end of the unit body by 1 mm to 5 mm, in order to ensure the silicon pad is in air seal contact with the cartridge.

5. The pneumatic injection device according to claim 1, wherein the output pressure selector is a three-way valve having an air conduit for passage of the air, and a turning adjustor in communication with the air conduit for providing the desirable pressure of the air that comes into the injection unit.

6. The pneumatic injection device according to claim 5, wherein the turning adjustor is formed as a cylindrical valve having air tracts of different sizes in operable communication with the air conduit for controlling the air at different pressures.

7. The pneumatic injection device according to claim 5, wherein the output pressure selector is disposed such that the tuning adjustor is manipulated by a finger.

8. The pneumatic injection device according to claim 1, wherein the input pressure adjustor comprises a pressure gauge and a pressure adjustment element for adjusting the pressure of the compressed air to a desirable range.

9. The pneumatic injection device according to claim 1, wherein the input end of the input pressure adjustor comprises a plug and play tubing connector for connection to the air outlet of the dental chair is a plug and play connector.

10. The injection device according to claim 1, wherein a control unit is arranged on the unit body of the injection unit for controlling flow rate and pressure of the compressed air that flows into the injection unit.

11. The pneumatic injection device according to claim 1, wherein the connections among the unit body of the injection unit, the air seal adaptor, the output pressure selector, the air releasing unit and the input pressure adjustor are accomplished in a threaded manner or in a plug and play manner.

12. The pneumatic injection device according to claim 1, wherein standard cartridges and needles are used as the cartridge and the needle of the pneumatic injection device.

13. A pneumatic injection device adapted to be connected with an air outlet of a dental chair for providing a compressed air flow, comprising:
- an injection unit comprising a unit body having a proximal end, a distal end and a cavity between the proximal and distal ends for receiving a dental cartridge, wherein the distal end has an injection needle connector for connecting a needle, and the proximal end is connected to an air seal adaptor in an airtight relationship;
- an output pressure selector having an output end connected air-tightly to the other end of the air seal adaptor, wherein the output pressure selector is a three-way valve having an air conduit for passage of the air, and a turning adjustor in communication with the air conduit for providing the desirable pressure of the air that comes into the injection unit, wherein the turning adjustor is formed as a cylindrical valve having air tracts of different sizes in operable communication with the air conduit for controlling the air at different pressures;
- an air releasing means having an output end connected air-tightly to an input end of the output pressure selector; and
- an input pressure adjustor having an output end connected air-tightly to an input end of the air releasing means, an input end for connection to the air outlet of the dental chair.

* * * * *